USOO5700657A

United States Patent [19]
Beaudry et al.

[11] Patent Number: 5,700,657
[45] Date of Patent: Dec. 23, 1997

[54] VECTORS AND VECTOR SYSTEMS INCLUDING GENES ENCODING TUMOR SUPPRESSOR PROTEINS AND PRODUCER CELLS TRANSFORMED THEREBY

[75] Inventors: Gary A. Beaudry, Montclair; Arthur H. Bertelsen, Ridgewood; Michael I. Sherman, GlenRidge, all of N.J.; Bert Vogelstein, Baltimore, Md.

[73] Assignee: Genzyme Corporation, Framingham, Mass.

[21] Appl. No.: 166,297

[22] Filed: Dec. 13, 1993

[51] Int. Cl.$^6$ .......................... C12P 21/02; C12P 19/34; C12N 5/10; C12N 7/01

[52] U.S. Cl. ................. 435/69.1; 435/91.33; 435/235.1; 435/325

[58] Field of Search ..................... 435/69.1, 69.2, 435/172.1, 172.3, 320.1, 240.2, 235.1, 325, 91.33, 91.3, 91.31, 91.32

[56] References Cited

U.S. PATENT DOCUMENTS 4,966,847  10/1990  McCormick et al. .............. 435/69.51
5,087,617  2/1992  Smith ........................... 514/44

FOREIGN PATENT DOCUMENTS

WO93/10814  6/1993  WIPO.
WO94/06910  3/1994  WIPO.

OTHER PUBLICATIONS

Bosselman et al. "Replication–Defective Chimeric Helper Proviruses and Factors Affecting Generation of Competent Virus: Expression of Moloney Murine Leukemia Virus Structural Genes via the Metallothionein Promoter", Mol. Cell. Biol., May 1987, pp. 1797–1806, vol. 7, No. 5.

Chen et al. "Genetic Mechanisms of Tumor Suppression by the Human p53 Gene", Science, vol. 250, Dec. 1990, pp. 1576–1580.

*Primary Examiner*—David Guzo
*Attorney, Agent, or Firm*—E. M. Olstein; R. J. Lillie

[57] ABSTRACT

Vectors and vector systems are embodied that include a gene encoding a tumor suppressor protein. In one embodiment, the vector includes a gene encoding a tumor suppressor protein and an inducible promoter controlling the gene encoding a tumor suppressor protein. The tumor suppressor protein may be p53 protein. In another embodiment, there is provided a vector system which comprises a first vector including a gene encoding a tumor suppressor protein, and a second vector containing a nucleic acid sequence encoding an antisense sequence complementary to all or a portion of the gene encoding a tumor suppressor protein. In yet another embodiment, there is provided a vector system which comprises a first vector including a gene encoding a tumor suppressor protein, and a second vector containing a gene which encodes a protein which binds to, and thereby inhibits, the tumor suppressor protein. Such vectors and vector systems enable cells transformed thereby to continue to proliferate such that adequate amounts of infectious viral particles, generated from viral vectors including a gene encoding a tumor suppressor protein, can be harvested for administration to patients.

8 Claims, No Drawings

VECTORS AND VECTOR SYSTEMS INCLUDING GENES ENCODING TUMOR SUPPRESSOR PROTEINS AND PRODUCER CELLS TRANSFORMED THEREBY

This invention relates to vectors and vector systems including tumor suppressor genes or their cDNA's and proteins encoded by them (hereinafter "tumor suppressor proteins"). The term "tumor suppressor gene" as used herein means a structural gene or the corresponding cDNA, or combinations of portions of each, that might be effective in reducing or eliminating the transformed or malignant phenotype of a cancer cell or inhibiting the growth of cancer cells or in other particular embodiments as described below. More particularly, this invention relates to vectors and vector systems including genes encoding tumor suppressor proteins which enable cells transformed thereby to continue to proliferate such that adequate amounts of such expression vectors and vector systems can be harvested for administration to patients.

Evidence suggests that many tumors have undergone loss or mutation of the p53 tumor suppressor gene (Baker, et al., *Science*, Vol. 244, pgs. 217–221 (1989)). Studies also have been published which demonstrate that introduction of the wild-type p53 gene into cells which have lost function of that gene can eliminate the transformed/malignant phenotype (Baker, et al., *Science*, Vol. 249, pg. 912 (1990). Thus, gene therapy with the p53 gene can be envisaged as a useful therapeutic approach to cancer, particularly for patients with tumors lacking p53 function.

In order to carry out gene therapy with p53, the p53 gene must be introduced into tumor cells. Such gene may be introduced into cancer cells in the absence of a biological delivery system, or be administered via an expression vector, such as, for example, a viral vector. The viral vector may be, for example, a retroviral vector. In order to generate adequate levels of virus containing the p53 gene, it is necessary to produce such virus in one or more producer cell lines. Examples of packaging and producer cell lines are described in Cepka, in *Current Protocols in Molecular Biology*, Ausubel, et al. (ads.) Chapter 9, pgs. 9.10.1–9.14.3. One difficulty that may be encountered in efforts to produce large amounts of such a recombinant virus is that the p53 gene in the virus may be transcribed and translated in the producer cells, leading to overproduction of p53 protein and consequent slowing or arrest of cell division (Baker, 1990 and Diller, et al., *Mol. Cell. Biol.*, Vol. 10, pgs. 5772–5781 (1990)). This, in turn, could hinder production of the numbers of cells needed to produce adequate amounts of virus. Also, spontaneous mutation of a wild-type p53 gene could promote growth of the cells carrying the mutated p53 gene such that these cells overgrow the ones carrying the wild-type gene. This would lead to selection of cells containing a mutated p53 gene in the viral population (Baker, 1990).

It is therefore an object of the present invention to provide means for generating sufficient numbers of producer cells containing vectors carrying genes encoding tumor suppressor proteins, such as p53 protein. It is also an object of the present invention to prevent cells carrying virus expressing a wild-type p53 gene from being overgrown by cells carrying virus with a mutated p53 gene.

In accordance with the present invention, there is provided a producer cell for producing a viral particle containing a viral vector including DNA or RNA encoding a tumor suppressor protein (for example, wild-type p53 protein) wherein the producer cell further includes an agent that prevents production of the tumor suppressor protein in the producer cell or inactivates the expressed tumor suppressor protein. The agent, for example, may be a promoter that does not promote transcription of the tumor suppressor gene under the conditions under which the producer cell proliferates and/or is maintained and/or an agent that prevents translation of mRNA encoding the tumor suppressor protein and/or an agent that binds to the tumor suppressor protein and inactivates such tumor suppressor protein.

In accordance with one aspect of the present invention, the producer cells are transduced with a vector, such as a viral vector, for example, that includes a gene encoding a tumor suppressor protein, and said gene being under control of an inducible promoter controlling transcription of the gene encoding the tumor suppressor protein. Examples of such inducible promoters include, but are not limited to, those described in Kriegler, Gene Transfer and Expression, a Lab Manual, pgs. 16–18 (1990) and Staeheli, *Adv. Virus Res.*, Vol. 38, pgs. 147–200 (1990).

The producer cells are grown under conditions that will not activate the inducible promoter (e.g., in the absence of an exogenous agent that activates the inducible promoter) such that tumor suppressor protein is not produced or is produced only in minimal quantities. Thus, the producer cells are able to proliferate and to generate recombinant viral particles, such as retroviral particles, adenoviral particles, or adeno-associated viral particles. Examples of retroviral particles that may be employed include, but are not limited to, those derived from Rous Sarcoma Virus, Harvey Sarcoma Virus, Moloney Murine Sarcoma Virus and Moloney Murine Leukemia Virus. Examples of retrovial vectors which may be employed include, but are not limited to, those described in Kriegler (1990) pgs. 23–61. Once such viral particles are generated, the viral particles may then be introduced into tumor cells. Thus, the inducible promoter must be one that is capable of being activated in target cells, such as cancer cells.

Examples of inducible promoters include, but are not limited to, metallothionein promoters, mouse mammary tumor virus (MMTV) promoter, interferon response element-containing promoters, lac operator-containing promoters, heat shock promoters and other hormone-responsive promoters. It is to be understood, however, that the scope of the present invention is not to be limited to any specific inducible promoter.

As hereinabove stated, the producer cells are grown under conditions that will not activate the inducible promoter. Thus, for example, in one embodiment when a metallothionein promoter is employed, the producer cells are grown in serum-free medium lacking trace metals because metallothionein promoters can be induced by trace metals found in serum. In another embodiment, when a hormone promoter is employed, the producer cells are grown in a medium that lacks such hormones.

By employing an inducible promoter, one can control the expression of the gene encoding a tumor suppressor protein, such that producer cells containing the vector may proliferate in the absence of tumor suppressor gene expression such that adequate amounts of viral particles generated from the producer cell containing the vector may be harvested for administration to patients. The tumor suppressor gene can be expressed in patients upon exposure to endogenous inducers (such as trace metals or other factors found in serum for a metallothionein promoter or hormones for hormone-inducible promoters) or upon administration of exogenous inducers to the patients (e.g., allolactose for the lac operator-containing promoters).

In one embodiment, the gene encoding a tumor suppressor protein encodes p53 protein. In other embodiments, tumor suppressor genes encoding tumor suppressor proteins include, but are not limited to, genes for retinoblastoma protein (Rb), "deleted in colorectal carcinoma" protein (DCC), adenomatous polyposis coli protein (APC), "mutated in colorectal carcinoma" protein (MCC), Wilm's tumor 1 protein (WT1), neurofibromatosis type 1 protein (NF1), or neurofibromatosis type 2 protein (NF2) (Marx, Science, Vol. 261, pg. 1385–1387 (1993)), or von Hippel-Lindau Disease protein (Latif, et al., Science, Vol. 260, pgs. 1317–1320 (1993)).

In accordance with another aspect of the present invention, the producer cells are transduced with a vector system that comprises a first vector including a gene encoding a tumor suppressor protein. The system also comprises a second vector containing a nucleic acid sequence which inhibits expression of the gene encoding a tumor suppressor protein or which inhibits the protein directly. Such nucleic acid sequence is sometimes hereinafter referred to as a "counteractive nucleic acid sequence."

In one embodiment, the counteractive nucleic acid sequence which inhibits expression of the gene encoding a tumor suppressor protein is a nucleic acid sequence encoding an antisense sequence complementary to all or a portion of the gene encoding a tumor suppressor protein.

In another embodiment, the counteractive nucleic acid sequence is a ribozyme-containing RNA that cleaves the mRNA of the tumor suppressor gene. In yet another related embodiment, the counteractive nucleic acid sequence is a DNA or RNA that can form a triplex structure with part or all of the tumor suppressor gene, thereby blocking transcription of the said gene. In yet another related embodiment, the counteractive nucleic acid sequence binds to the protein product of the tumor suppressor gene, thereby interfering with its function.

The first vector may be a viral vector such as those hereinabove described, that is capable of being packaged into a viral particle. The tumor suppressor protein also may be selected from those hereinabove described.

The second vector, which contains the counteractive nucleic acid sequence that can be transcribed or reverse-transcribed to produce a nucleic acid that blocks expression of the tumor suppressor gene or its mRNA or that blocks the activity of the tumor suppressor protein, is a vector that is not a viral vector or a vector that is defective such that it is not packaged into a viral particle.

Thus, when the producer cells are transduced with the first and second vectors of the vector system, expression of the tumor supressor gene into tumor suppressor protein is blocked by the counteractive nucleic acid sequence in the second vector either by inhibiting tumor suppressor gene transcription into mRNA or by inhibiting translation or processing of the tumor suppressor gene mRNA. The counteractive nucleic acid sequence that encodes an antisense or ribozyme or triplex sequence complementary to all or a portion of the gene encoding a tumor suppressor protein in its general contains as little as about 15 bases of the tumor suppressor gene sequence to as much as the entire tumor suppressor gene sequence. Because only the first vector of the vector system is packaged into a viral particle, such viral particle may transduce or be otherwise caused to enter a tumor cell, and the tumor suppressor protein is expressed in the tumor cell, whereby the malignant phenotype of the tumor cell is eliminated.

In an alternative embodiment, the counteractive nucleic acid sequence can be included in the same viral vector as the tumor suppressor gene but can be placed under control of an inducible promoter or repressor such that the expression of the counteractive nucleic acid sequence can be controlled to occur only during production of the vital vector from the producer cell line. Thus, the promoter controlling transcription of the counteractive nucleic acid sequence would be inactive after the virus vector was administered to a patient. One such example is the lac operator-containing promoter that is under control of lac repressor protein and induced by, for example, the compound isopropylthio-β-galactoside, or IPTG.

In accordance with yet another aspect of the present invention, the producer cells are transduced with a vector system comprising a first vector including a gene encoding a tumor suppressor protein, and a second vector containing a gene that encodes a protein (the "counteractive protein") that binds to, or otherwise counteracts the function of, the tumor suppressor protein.

The first vector may be a viral vector such as those hereinabove described and may be packaged into viral particle. The second vector, however, is not a viral vector or is a defective viral vector that is not packaged into a viral particle.

Thus, in the producer cells containing the first and second vectors, the tumor suppressor protein expressed by the first vector is bound or otherwise counteracted by the protein expressed by the second vector. Thus, the tumor suppressor protein will not affect the growth of the producer cells. Because only the first vector is packaged into a viral particle, such viral particle does not include the gene encoding a counteractive protein. Thus, the viral particle may be employed in transducing or otherwise being caused to enter tumor cells in order to eliminate the malignant phenotype thereof.

Proteins that bind to, for example, the p53 tumor suppressor protein include, but are not limited to, MDM-2 protein, SV40 T antigen, HPV E6 protein, HPV E6-associated protein, adenoviral E1b protein, TATA binding protein (such as described in Pietenpol, et al., Nature, Vol. 365, pgs. 17–18, (1993)) and antibody that binds p53, such as a single-chain antibody. Such protein may be produced in adequate amounts to bind to, and thereby prevent, the function of the p53 tumor suppressor protein in the producer cells. Similarly, examples of proteins that bind to and prevent function of the Rb tumor suppressor protein include, but are not limited to, SV40 T antigen, adenovirus E1a and HPV E7.

Further examples of counteractive proteins are mutated or otherwise altered versions of the tumor suppressor proteins. As an example, one counteractive protein for wild-type p53 is a mutated version of p53 that fails to bind the DNA sequence to which wild-type p53 protein binds, but oligomerizes with wild-type p53, such complexes failing to bind DNA. Such mutated proteins are well known in the art. Similarly, other counteractive proteins for wild-type p53 are partial fragments of the p53 protein containing the oligomerization site; aggregates containing wild-type p53 and such fragments fail to bind the p53-binding DNA sequence (Shaulian, et al., Mol. Cell. Biol., Vol. 12, pgs 5581–5582 (1992)). Similarly, in another example, a truncated N-terminal portion of the APC tumor suppressor protein apparently blocks function of the APC tumor suppressor protein (Su, et al., Cancer Res., Vol. 53, pgs. 2728–2731 (1993)).

In one embodiment, the second vector further includes an inducible promoter controlling the gene that encodes the protein that counteracts the tumor suppressor protein. The inducible promoter may be selected from those hereinabove described. Thus, expression of the counteractive protein that is controlled such that the counteractive protein is produced on an "as-needed" basis; i.e., the counteractive protein is produced when one desires to prevent the tumor suppressor protein from functioning in the producer cells.

In yet another aspect of this invention, the producer cells are transduced or transfected with a vector system comprising a first vector including a gene encoding a p53 tumor suppressor protein, and a second vector containing a counteractive nucleic acid sequence that contains multiple DNA-binding sites for the p53 protein. The first vector may be a viral vector such as those hereinabove described and may be packaged into a viral particle. The second vector, however, is not a viral vector or is a defective viral vector that is not packaged into a viral particle. Thus, in producer cells containing the first and second vectors, the p53 tumor suppressor protein expressed by the first vector is sequestered by the p53 cognate DNA-binding sequences in the second vector and p53 function is inhibited (European Patent Application No. 88307302.5 (1988)), preventing growth inhibition of the producer cells.

In a related embodiment of this invention, the producer cells are transduced or transfected with a vector system comprising a first vector including a gene encoding a p53 tumor suppressor protein and a second vector containing a counteractive nucleic acid sequence, or a nucleic acid sequence encoding a counteractive protein. The expression from the second vector is designed to be under the control of the p53 tumor suppressor protein by containing one or more cognate DNA binding sites for the p53 protein. (Kern, et al., Science, Vol. 256, pgs. 827–830 (1992); El Deiry, et al., Nature Genetics, Vol. 1, pgs. 45–49 (1992)). The first vector may be a viral vector such as those hereinabove described and may be packaged into a viral particle. The second vector, however, is not a viral vector or is a defective viral vector that is not packaged into a viral particle. Thus, in producer cells containing the first and second vectors, when p53 tumor suppressor protein is produced, transactivation of genes encoding counteractive nucleic acids or counteractive proteins will occur. Such counteractive nucleic acids or counteractive proteins will sequester p53 tumor suppressor protein function, and consequently growth of the producer cells will not be inhibited.

In yet another embodiment of this invention, the producer cells are transduced or transfected with a vector system comprising both a gene encoding a tumor suppressor protein, and a second gene encoding a counteractive protein, the expression of such second gene being under the control of an inducible promoter or repressor such that the production of the counteractive protein occurs only during production of the viral vector. Thus, the promoter would be inducible by agents not encountered after the virus vector is administered to the patient. One such example is the bacterial lac operator promoter that is under control of the compound IPTG.

It is desirable that the counteractive nucleic acid sequences or proteins described hereinabove be produced in amounts adequate to inhibit the function of the tumor suppressor protein. Such high level expression can be achieved by using strong transcriptional control sequences that are generally expressed at high levels. Alternatively, the high level expression might be limited to cells of a particular tissue type. A discussion of cell type-specific promoter and enhancer control sequences can be found in Kriegler, M., 1990, pgs. 3–22 and in Korfhagen, et al., Proc. Nat. Acad. Sci., Vol. 87, pgs. 6122–6126 (1990). Other strong tissue-specific or tissue-independent promoters can be used to promote high levels of expression of a counteractive nucleic acid sequence or a gene encoding a counteractive protein.

In yet another embodiment of this invention, viral producer cells are constructed to permit viral particle generation (Miller, et al., Biotechniques, Vol. 7, No. 9, pgs. 980–990 (1989)) from cells that produce endogenously adequate amounts of the counteractive nucleic acid sequence or gene encoding a counteractive protein such that minimal amounts of the tumor suppressor protein are produced or such that the function of the tumor suppressor gene product is inhibited. Examples of such cells include, but are not limited to, ZR-75 and MCF-7 breast carcinoma cells, (Sheikh, et al., Cancer Res., Vol. 53, pgs 3226–3228 (1993)) OsA-CL osteosarcoma cells, (Oliner, et al., Nature, Vol. 358, pgs. 80–83 (1992)), and 3T3 DM cells (Fakharzedeh, et al., EMBO J., Vol. 10, No. 6, pgs. 1565–1569 (1991)), that have been observed to produce high levels of MDM2 protein. Such cells could be made to serve as producer cells for the production of viral particles containing p53 tumor suppressor gene.

In yet another embodiment of the present invention it may be advantageous to generate viral producer cell lines from host cells that contain only wild-type p53 gene sequences or alternatively that contain no p53 genes. A producer cell line that is derived from a cell with no endogenous p53 genes or with only wild-type p53 genes has a potential advantage over one derived from a cell carrying (a) mutant p53 allele(s). The wild-type p53-containing cells or those devoid of p53 genes cannot undergo homologous recombination with the p53 gene of the recombinant vector to generate a mutant p53 gene that might be packaged into recombinant virions.

The viral particles containing genes encoding tumor suppressor protein as described hereinabove, once generated, are transduced or otherwise caused to enter into benign or malignant tumor cells such as those from tumors of the colon, rectum, lung, breast, prostate, kidney, brain, skin, eye, lymph or any other organ or tissue or blood cells. The viral particles, once generated, are transduced or otherwise caused to enter into benign or malignant tumor cells whether or not said cells are deficient in the production of the tumor suppressor protein encoded in the virus particle since such transduction could serve to slow growth in tumor cells by resulting in overproduction of tumor suppressor protein. Similarly, the viral particles, once generated, are transduced or otherwise caused to enter into non-tumor cells which are growing in an undesirable manner including, but not limited to, warts of the skin, genital warts or blood cells. In yet another embodiment, the viral particles, once generated, are transduced or otherwise caused to enter into cells, such as tumor cells, to be used to administer to patients to generate a desired response such as an immune response, when the objective is that the aforesaid cells should proliferate rarely, if at all, upon said transfer into patients. The transfected tumor cells then are exposed to an inducer, whereby the tumor suppressor protein is expressed by the transfected cells whereby growth or another undesirable characteristic of the cells, such as spread to a second site, is prevented.

The above-described embodiments all relate to the production of recombinant viral vectors that encode tumor suppressor gene products that are cytotoxic or cytostatic for the producer cell line. The invention describes methods to circumvent this cytotoxic/cytostatic property of the virus-encoded gene product. It is envisaged that similar uses of the invention could be applied to the production of recombinant vectors encoding proteins that are not tumor suppressors but that share this cytotoxic/cytostatic property.

The invention will now be described with respect to the following examples; however, the scope of the present invention is not intended to be limited thereby.

EXAMPLE 1

A. Production of a producer cell line expressing high levels of mutant p53

Expression vectors have been constructed for efficient expression of mutant p53 in mammalian cell lines (Baker, et al., *Science*, Vol. 249, pgs. 912–915, (1990)). These expression vectors contain the CMV promoter/enhancer sequences which drive expression of p53 and splicing and polyadenylation sites derived from the rabbit beta globin gene. In addition, the vector confers geneticin resistance through expression of the neomycin resistance gene under separate control of an HSV thymidine kinase promoter.

The cell lines utilized for production of recombinant retroviruses are, but are not limited to, PE501 (ecotrophic producer), and PA317 (amphotrophic producer). To produce high levels of mutant p53 in PE501 or PA317 cells, the p53 expression vectors are co-transfected with a plasmid containing a dominant selectable marker capable of gene amplification: pSV2ADA, adenosine deaminase; pSV2GS, glutamine synthetase; or pSV2dhfr, dihydrofolate reductase. Typically, cells are transfected with a 1000:1 molar ratio of p53 expression plasmid:plasmid containing the amplifiable gene. Approximately 3–5 days post transfection, cells are placed in the appropriate selective medium. Approximately 10–15 days post selection, individual cell clones are picked and analyzed for stable expression of p53. Clones that express the highest levels of mutant p53 (as assessed by standard Western blotting or immunoprecipitation procedures) are subjected to selection for amplification of the selectable marker by methods that are well-established in the art. Cells surviving increasing selective pressure are analyzed to identify those with the highest levels of mutant p53 expression, the increased levels of expression resulting from co-amplification of the mutant p53 gene when the selected marker was amplified.

B. Production of a producer cell line expressing high levels of p53 miniprotein Functional p53 is generally believed to exist as a dimer or a tetramer. The domains of p53 responsible for these protein-protein interactions have been mapped to the carboxyl terminus of p53 (Sturzbecher, H. et al., *Oncogene*, Vol. 7, pgs. 1513–1523, 1992). Miniproteins consisting of approximately 60–100 amino acids from the carboxyl terminus of p53 have been demonstrated to complex with full-length p53 and cause an inactivation of p53 function (Shaulian, et al, *Molec. Cell. Biol.*, Vol. 12, pgs. 5581–5592, 1992). Genes encoding such miniproteins are synthesized to include an amino-terminal methionine codon that can serve to initiate protein translation for the miniprotein gene. The resulting genes are cloned into the expression plasmid as described in Section (A). The resulting miniprotein expression plasmids are transformed into, and amplified in, the producer cells as described above.

C. Production of a producer cell line expressing high levels of a p53 inactivating protein The rationale for expressing elevated levels of a p53 inactivating protein is that the inactivating protein binds and sequesters p53, thereby causing an inactivation of p53 function. Several proteins, most notably MDM-2, have been described to function in this manner. However, other proteins, such as certain antibodies to p53, may also inactivate p53 function. Cloning of the inactivating protein, transfection of cells, amplification of the appropriate gene, and analysis of the expression of the gene encoding the inactivating protein are as described in Section (A) for mutant p53. Because high level expression of the inactivating protein may be toxic to cells expressing the particular protein (in the absence of p53) it may be desirable to regulate the expression of this particular protein. One method for regulating expression of the inactivating protein is to clone the inactivating protein in an expression plasmid which contains a minimal promoter sequence and a cognate DNA binding site for p53 protein to the 5' side of the inactivating protein structural gene. In this manner, efficient expression of the inactivating protein occurs only when p53 protein is present (i.e., when the p53-gene-containing retrovirus is being produced).

EXAMPLE 2

A. Production of a producer cell line expressing high levels of antisense p53

Stable and effective (>95%) antisense RNA mediated inhibition of gene expression has been demonstrated for endogenous cell proteins (Hambor, et al., *PNAS* Vol. 85, pgs. 4010–4014, 1988). Plasmids expressing antisense RNA are generated by inserting the entire p53 cDNA or fragments of the p53 cDNA into an expression plasmid (e.g., the plasmid of Example 1, Section (A), or in the plasmid in Hambor, et al., 1988 such that the coding strand is in a 3' to 5' orientation relative to the location of the transcriptional promoter sequence. In this manner, the RNA which is produced by transcription of the inserted DNA will be complementary to the RNA produced from a p53 expression plasmid. The antisense plasmid is transformed into and amplified in the producer cells as described in Example 1, Section (A). Since the antisense RNA is highly amplified in the producer cells, each cell contains many more copies of the antisense RNA which causes a hybridization arrest of translation of p53 protein.

B. Production of a producer cell line containing multiple copies of a p53 DNA-binding site for p53 protein It has been established that wild-type p53 is a sequence-specific DNA-binding protein, and that p53 functions to regulate the transcription of genes that contain a p53-binding DNA sequence. A systematic study of the binding site recognized by p53 in vitro has identified a potent p53-binding DNA sequence (Halazonetis, T., et al., *EMBO J.*, Vol. 12, pgs. 1021–1028, 1993). The goal of inserting multiple 'artificial binding sites' that have high affinity for p53 into the producer cells is to compete with those p53 DNA-binding sequences that are responsible for controlling the transcription of genes that regulate cell growth. If these artificially introduced p53 DNA-binding sites effectively compete for all available p53, then the growth of producer cells will be unaffected and the cells will produce a high titre of recombinant p53 gene-containing retrovirus.

Construction of a plasmid with multiple p53 DNA-binding sequences (DBS) would facilitate competition with cellular p53 DBS. Synthetic oligonucleotides containing the optimal p53 DBS as described by Halazonetis, et al. (op. cit.) are synthesized, ligated, and cloned such that multiple copies of the DBS are contained in the plasmid. Plasmids that contain multiple p53 DBS have been described (Kern, S. et al., *Science*, Vol. 236, pgs. 827–830, 1992). Producer cells are co-transfected with the p53 DBS containing plasmid along with a plasmid containing an amplifiable gene as described in Example 1, Section (A). Identification of clones and amplification of the integrated genes contained within the clones is carried out by well established procedures as described in Example 1, Section (A).

Alternatively, the multiple p53 DBS is cloned in an episomal vector such as the pREP or pMEP series (Invitrogen) which has been modified to replace the promoter/enhancer and polyadenylation sequences with the multiple p53 DBS. These recombinant plasmids differ from those described by Kern, et al. (1992) in that they are non-integrating and maintained extrachromosomally at high copy number.

EXAMPLE 3

Production of a producer cell line expressing high levels of antisense DCC

Narayanan, et al., *Oncogene*, Vol. 7, pgs. 553–561 (1992) have described an antisense construct that can be used to block expression of the DCC gene, resulting in acceleration of cell growth. Plasmids expressing a 357 base pair DCC antisense construct under control of a dexamethasone-inducible promoter as well as a neomycin-resistance gene are transfected into producer cells. G418-resistant colonies are selected, and expression of DCC antisense RNA is confirmed, all as described by Narayanan, et al. (1992). Because the antisense RNA can be induced to high levels in the producer cells upon treatment with dexamethasone, each cell contains many copies of the antisense RNA which causes a hybridization arrest of translation of DCC protein. This in turn blocks the growth-inhibitory effect of DCC protein.

EXAMPLE 4

Generation of a producer cell line requiring wild-type p53 expression

In the preparation of recombinant p53 expression vectors for therapeutic uses, it is advantageous to avoid the production of a spontaneously mutated p53 gene that confers a dominant-negative phenotype to the p53 protein. Such a mutation might be expected to confer a selective advantage on the producer cell in which it arises such that this producer cell would overgrow the non-mutated producer cells making wild-type p53 protein and vector. To avoid such a situation, it is useful to prepare a producer cell line that expresses a selectable marker gene under control of a minimal promoter augmented by a p53 DBS. Thus, the expression of the selectable marker would require the continuous presence of a wild-type p53 protein to transactivate the minimal promoter.

To construct the producer cell line, a suitable p53 "null" cell is transformed with an expression vector that encodes a first selectable marker (e.g., a hygromycin resistance gene) under control of a promoter such as the HSV thymidine kinase promoter as well as a second selectable marker under the control of a p53 DBS minimal promoter constructed as described above. Cells are selected for the presence of the first marker and then tested for expression of the second marker gene by Northern blotting following transient transfection with a wild-type p53 expression vector. Cells expressing RNA for the second marker are then used to generate retroviral producer lines for wild-type-p53 expressing recombinant retroviruses.

A vector carrying the gene for wild-type p53 is used to transduce the amphotrophic cell line expressing the first selectable marker and selection for the second selectable marker is performed. Resistant cells are cloned and evaluated for recombinant virus production. High level expressing clones are identified and grown to generate producer lines.

Continuous selection using the second selectable marker during production of recombinant virus stocks would prohibit the outgrowth of cells sustaining dominant-negative mutations in their p53 transgene(s). Such mutations would block production of the second selectable marker rendering the cells unable to grow. This would ensure a virus stock with minimal content of mutant p53 genes.

EXAMPLE 5

Production of recombinant retrovirus expressing cytotoxic/cytostatic gene products The generation of a recombinant vector encoding a cytotoxic or cytostatic gene product whether or not such product is a known tumor suppressor gene product, can be envisaged to be a useful objective. As has been described, the production of such a vector in a producer cell line would be problematic if the functional cytotoxic or cytostatic gene product were expressed in the producer cell line. Application of the same strategies described for the prevention of tumor suppressor gene expression in producer lines to the prevention of expression of any cytotoxic or cytostatic gene product would allow these vectors to be produced. For example, WAF-1 is a gene encoding a 164 amino acid protein that is induced by expression of wild-type p53 and results in the arrest of cell growth (El-Deiry, W. S., et al., *Cell*, Vol. 75, pgs. 817–825 (1993). In order to prepare a producer line capable of generating recombinant retrovirus encoding WAF-1, one approach is to engineer a cell line that expresses WAF-1 antisense RNA. PE501 cells are co-transfected with an expression vector encoding both a hygromycin resistance gene and the antisense RNA for WAF-1 expressed under control of the CMV Immediate Early promoter/enhancer and a plasmid containing a dominant selectable marker such as pSV$_2$dhfr. Co-transfection is performed as described in Example 1A. Hygromycin-resistant cells are tested for expression of WAF-1 antisense RNA by Northern blotting procedures and clones expressing WAF-1 antisense are subjected to selection for amplification of the dihydrofolate reductase gene by well established methods. Cells surviving increasing selective pressure (e.g., higher concentrations of methotrexate added to the culture medium) are analyzed by Northern blotting to identify those with the highest levels of WAF-1 antisense RNA, resulting from co-amplification of the WAF-1 antisense transgene. Cells expressing the highest levels of WAF-1 antisense RNA are used as producer cells for retroviral particles encoding WAF-1 protein. WAF-1 protein expression in the producer cells transduced with recombinant retroviral vector is blocked by hybridization-arrested translation due to the constitutive high level expression of the WAF-1 antisense RNA.

All publications cited herein are hereby incorporated by reference.

It is to be understood, however, that the scope of the present invention is not to be limited to the specific embodiments described above. The invention may be practiced other than as particularly described and still be within the scope of the accompanying claims.

What is claimed is:

1. A process for producing a retroviral vector particle in a producer cell comprising:
    producing a retroviral vector particle from a producer cell containing a retroviral vector including RNA or DNA encoding a tumor suppressor protein wherein expression of said tumor suppressor protein is controlled by an inducible promoter and said retroviral vector particle is produced under conditions under which the inducible promoter is not activated.

2. The process of claim 1 wherein said tumor suppressor protein is selected from the group consisting of p53 protein;

DCC protein; APC protein, MCC protein; WT1 protein; NF1 protein; and NF2 protein; and von Hippel-Lindau disease protein.

3. The process of claim 1 wherein said minor suppressor protein is the p53 protein.

4. The process of claim 3 wherein said inducible promoter is selected form the group consisting of metallothionein promoters, mouse mammary tumor virus promoter, interferon response element-containing promoters, lac operator—containing promoters, heat shock promoters, and hormone-responsive promoters.

5. The process of claim 4 wherein said promoter is a metallothionein promoter and said producer cells are grown in a medium lacking trace metals.

6. The process of claim 4 wherein said promoter is a hormone-responsive promoter and said producer cells are grown in a medium lacking said hormone which induces said hormone-responsive promoter.

7. A producer cell for producing a retroviral vector particle, said producer cell containing DNA or RNA encoding a tumor suppressor protein and an inducible promoter controlling expression of said DNA or RNA encoding said tumor suppressor protein, wherein said tumor suppressor protein is not expressed under the conditions under which the producer cell is maintained.

8. The producer cell of claim 7 wherein said tumor suppressor protein is p53 protein.

* * * * *